(12) United States Patent
Hoang et al.

(10) Patent No.: US 12,725,679 B2
(45) Date of Patent: Sep. 1, 2026

(54) GENERATIVE MODELING AND REPRESENTATIONAL LEARNING FROM MULTI-SEQUENCE ALIGNMENT AND PHYLOGENETIC TREE DATA

(71) Applicant: International Business Machines Corporation, Armonk, NY (US)

(72) Inventors: Thanh Lam Hoang, Maynooth (IE); Marcos Martínez Galindo, Dublin (IE); Gabriele Picco, Dublin (IE); Mykhaylo Zayats, Dublin (IE); Nhan Huu Pham, Tarrytown, NY (US); Lam Minh Nguyen, Ossining, NY (US); Marco Luca Sbodio, Dublin (IE); Dzung Tien Phan, Pleasantville, NY (US); Vanessa Lopez Garcia, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 584 days.

(21) Appl. No.: 18/345,318

(22) Filed: Jun. 30, 2023

(65) Prior Publication Data

US 2025/0006306 A1 Jan. 2, 2025

(51) Int. Cl.
*G16B 40/00* (2019.01)
*G16B 10/00* (2019.01)

(52) U.S. Cl.
CPC ............. *G16B 40/00* (2019.02); *G16B 10/00* (2019.02)

(58) Field of Classification Search
CPC ................................ G16B 40/00; G16B 10/00
See application file for complete search history.

(56) References Cited

U.S. PATENT DOCUMENTS

2013/0217006 A1 8/2013 Sorenson et al.
2021/0174246 A1 6/2021 Triplet
2021/0174903 A1 6/2021 Rothberg et al.
2021/0174906 A1* 6/2021 Ul Ain .................. G16B 25/00
2021/0287088 A1 9/2021 Peng et al.
(Continued)

FOREIGN PATENT DOCUMENTS

CN 112926629 A 6/2021
CN 112949850 A 6/2021
(Continued)

OTHER PUBLICATIONS

Cardona (Comparison of Tree-Child Phylogenetic Networks, IEEE, 2009, pp. 552-569) (Year: 2009).*
(Continued)

*Primary Examiner* — Oleg Korsak
(74) *Attorney, Agent, or Firm* — Yee & Associates, P.C.

(57) ABSTRACT

Generative modeling from phylogenetic data is provided. The method comprises creating a multi-sequence alignment (MSA) based on a nucleic acid or protein sequence and generating a phylogenetic tree based on the MSA. The phylogenetic tree is fed into a number of machine learning models, which generate vector representations of the nucleic acid or protein sequences based on the phylogenetic tree. The machine learning models generate from the vector representation predicted nucleic acid or protein sequences for at least one of an evolution sequence, regression sequence, or sibling sequences of nucleic acids or proteins according to the phylogenetic tree.

20 Claims, 8 Drawing Sheets

(56) References Cited

U.S. PATENT DOCUMENTS

| | | | | |
|---|---|---|---|---|
| 2022/0392566 | A1 | 12/2022 | Chatterjee et al. | |
| 2023/0207054 | A1* | 6/2023 | Rashid | G16B 20/20 706/21 |
| 2023/0307092 | A1* | 9/2023 | Senapathy | G16H 50/50 |

FOREIGN PATENT DOCUMENTS

| | | | |
|---|---|---|---|
| CN | 113269322 | A | 8/2021 |
| CN | 113723615 | A | 11/2021 |
| CN | 114114911 | A | 3/2022 |
| KR | 10-2022-0151257 | A | 11/2022 |
| WO | 2022/022816 | A1 | 2/2022 |
| WO | 2022112255 | A1 | 6/2022 |

OTHER PUBLICATIONS

Ding et al., "Deciphering protein evolution and fitness landscapes with latent space models", Nature Communications, vol. 10, Article 5644, 2019, pp. 1-13, accessed Jun. 28, 2023, https://www.nature.com/articles/s41467-019-13633-0.

Gascuel et al., "Predicting the Ancestral Character Changes in a Tree is Typically Easier than Predicting the Root State", Oxford Academic, Systematic Biology, vol. 63, Issue 3, May 2014, pp. 421-435, accessed Jun. 28, 2023, https://academic.oup.com/sysbio/article/63/3/421/2848633.

Layer et al., "Phylogenetic trees and Euclidean embeddings", Arxiv.org, May 3, 2016, pp. 1-12, accessed Jun. 28, 2023, https://arxiv.org/abs/1605.01039.

Matsumoto et al, "Novel metric for hyperbolic phylogenetic tree embeddings", Oxford Academic, Biology Methods & Protocols, vol. 6, Issue 1, 2021, pp. 1-11, accessed Jun. 28, 2023, https://academic.oup.com/biomethods/article/6/1/bpab006/6192799.

Pagel, "The Maximum Likelihood Approach to Reconstructing Ancestral Character States of Discrete Characters on Phylogenies", Oxford Academic, Systematic Biology, vol. 48, Issue 3, Jul. 1, 1999, pp. 612-622, accessed Jun. 28, 2023, https://academic.oup.com/sysbio/article/ 48/3/612/1641545.

Rao et al., "MSA Transformer", bioRxiv, Feb. 13, 2021, pp. 1-16, accessed Jun. 28, 2023, https://www.biorxiv.org/content/10.1101/2021.02.12.430858v1.

Salama et al, "The prediction of virus mutation using neural networks and rough set techniques", EURASIP Journal on Bioinformatics and Systems Biology, May 13, 2016, pp. 1-11, accessed Jun. 28, 2023, https://bsb-eurasipjournals.springeropen.com/articles/10.1186/s13637-016-0042-0.

Steipe et al., "Sequence Statistics Reliably Predict Stabilizing Mutations in a Protein Domain", Science Direct, Journal of Molecular Biology, vol. 240, Issue 3, Jul. 14, 1994, pp. 188-192, accessed Jun. 28, 2023, https://www.sciencedirect.com/science/article/abs/pii/S0022283684714343.

Zhu et al., "Applying Neural Network to Reconstruction of Phylogenetic Tree", ICMLC 2021: 2021 13th International Conference on Machine Learning and Computing, Feb. 2021, pp. 146-152, accessed Jun. 28, 2023, https://di.acm.org/doi/abs/10.1145/3457682.3457704.

Github. "Generative Toolkit 4 Scientific Discovery", retrieved from web https://web.archive.org/web/20230514071708/https://github.com/GT4SD, May 14, 2023, 4 pages.

Wikipedia. "Diagram", retrieved from web https://web.archive.org/web/20230507084252/https://en.wikipedia.org/wiki/Diagram, May 7, 2023, 7 pages.

Wikipedia. "Evolution", retrieved from web https://web.archive.org/web/20230504012905/https://en.wikipedia.org/wiki/Evolution, May 4, 2023, 83 pages.

Wikipedia. "Species", retrieved from web https://web.archive.org/web/20230511014806/https://en.wikipedia.org/wiki/Species, May 11, 2023, 31 pages.

Wikipedia. "Tree (graph theory)", retrieved from web https://web.archive.org/web/20230503032335/https://en.wikipedia.org/wiki/Tree_(graph_theory), May 3, 2023, 8 pages.

* cited by examiner

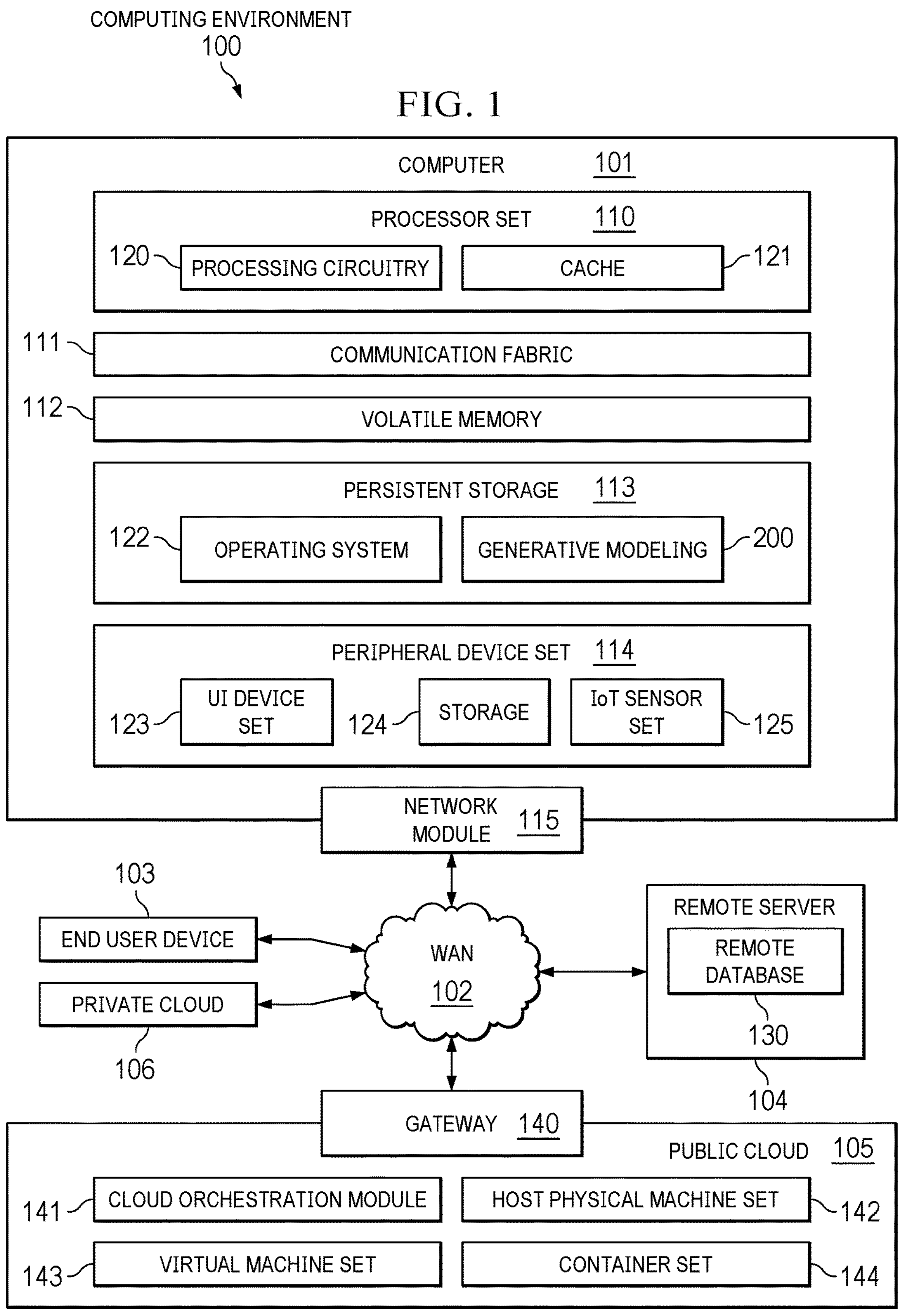
COMPUTING ENVIRONMENT
100
FIG. 1
COMPUTER 101
PROCESSOR SET 110
120
PROCESSING CIRCUITRY
CACHE
121
111
COMMUNICATION FABRIC
112
VOLATILE MEMORY
PERSISTENT STORAGE 113
122
OPERATING SYSTEM
GENERATIVE MODELING
200
PERIPHERAL DEVICE SET 114
123
UI DEVICE SET
124
STORAGE
IoT SENSOR SET
125
NETWORK MODULE 115
103
END USER DEVICE
PRIVATE CLOUD
106
WAN
102
REMOTE SERVER
REMOTE DATABASE
130
104
GATEWAY 140
PUBLIC CLOUD 105
141
CLOUD ORCHESTRATION MODULE
HOST PHYSICAL MACHINE SET
142
143
VIRTUAL MACHINE SET
CONTAINER SET
144

GENERATIVE MODELING AND REPRESENTATIONAL LEARNING FROM MULTI-SEQUENCE ALIGNMENT AND PHYLOGENETIC TREE DATA

BACKGROUND

The present disclosure relates generally to bioinformatics, and more specifically to prediction of nucleic acid or protein sequences according multi-sequence alignments and phylogenetic trees.

Multi-sequence alignment (MSA) is a bioinformatics technique used to align multiple sequences such as nucleic acid sequences (DNA, RNA) or protein sequences. MSA arranges sequences such that related positions across the sequences are aligned. This alignment can contribute to understanding function and structural properties of the sequences and inferring evolutionary relationships.

Phylogenetic trees are branching diagrams that depict evolutionary relationships among various biological species or other entities (e.g., protein sequences in a family) based upon similarities and differences in their physical or genetic characteristics.

SUMMARY

An illustrative embodiment provides a computer-implement method of generative modeling from phylogenetic data. The method comprises creating a multi-sequence alignment (MSA) based on a nucleic acid or protein sequence and generating a phylogenetic tree based on the MSA. The phylogenetic tree is fed into a number of machine learning models, which generate vector representations of the nucleic acid or protein sequences based on the phylogenetic tree. The machine learning models generate from the vector representation predicted nucleic acid or protein sequences for at least one of an evolution sequence, regression sequence, or sibling sequences of nucleic acids or proteins according to the phylogenetic tree. According to other illustrative embodiments, a computer system, and a computer program product for generative modeling from phylogenetic data are provided.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 1 depicts a pictorial representation of a computing environment in which illustrative embodiments may be implemented;

DETAILED DESCRIPTION

Figure 2:
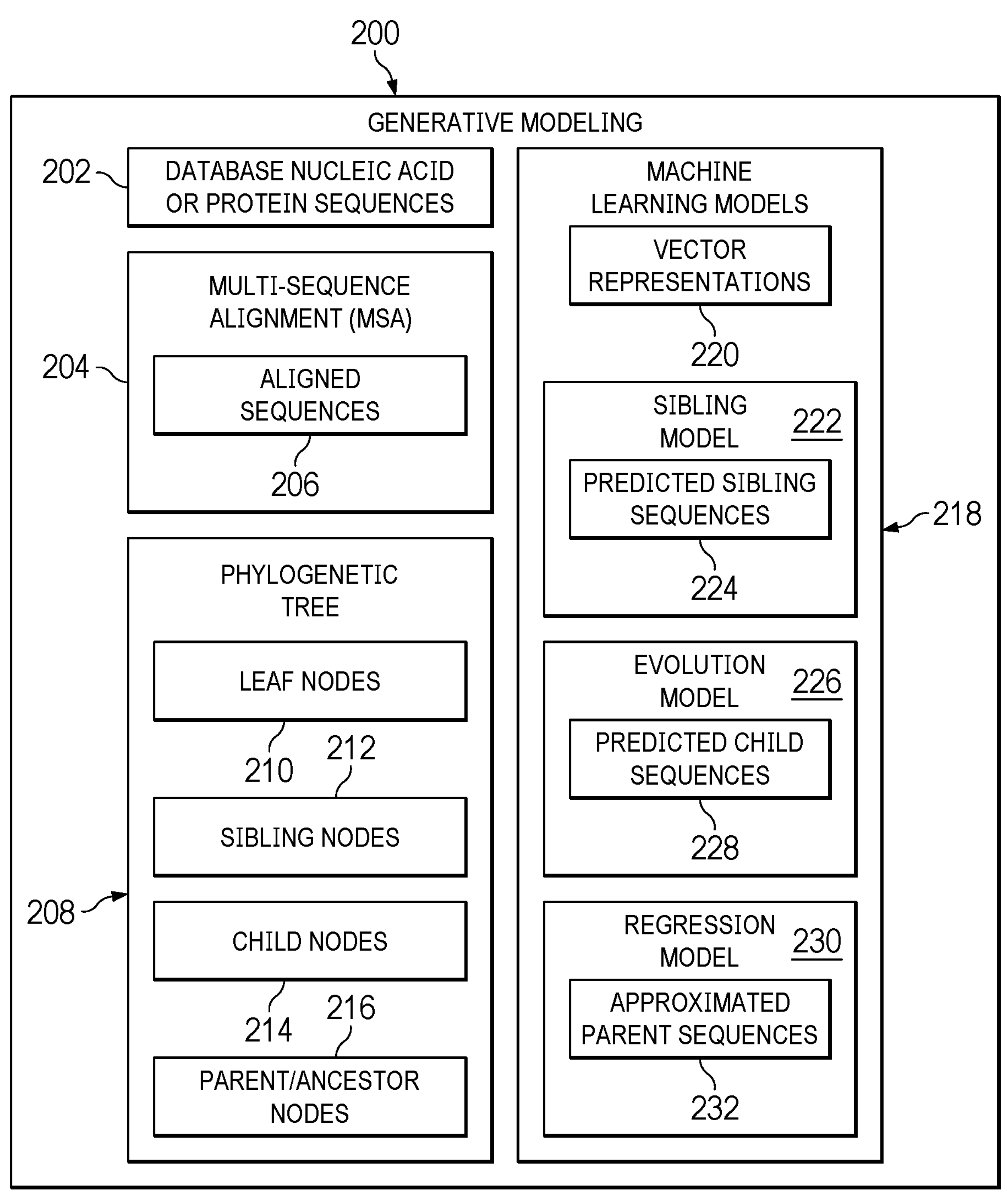
FIG. 2 depicts a block diagram for generative modeling from phylogenetic data in accordance with an illustrative embodiment.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc), or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

With reference now to the figures, and in particular, with reference to FIG. 1, a diagram of a data processing environment is provided in which illustrative embodiments may be implemented. It should be appreciated that FIG. 1 is only meant as an example and are not intended to assert or imply any limitation with regard to the environments in which different embodiments may be implemented. Many modifications to the depicted environment may be made.

FIG. 1 depicts a pictorial representation of a computing environment in which illustrative embodiments may be implemented. Computing environment 100 contains an example of an environment for the execution of at least some of the computer code involved in performing the inventive methods, such as generative modeling 200. In addition to generative modeling 200, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and generative modeling 200, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

Computer 101 may take the form of a desktop computer, laptop computer, tablet computer, smart phone, smart watch or other wearable computer, mainframe computer, quantum computer, or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

Processor set 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in generative modeling 200 in persistent storage 113.

Communication fabric 111 is the signal conduction path that allows the various components of computer 101 to communicate with each other. Typically, this fabric is made of switches and electrically conductive paths, such as the switches and electrically conductive paths that make up busses, bridges, physical input/output ports, and the like. Other types of signal communication paths may be used, such as fiber optic communication paths and/or wireless communication paths.

Volatile memory 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

Persistent storage 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data, and re-writing of data. Some familiar forms of persistent storage include magnetic disks and solid state storage devices. Operating system 122 may take several forms, such as various known proprietary operating systems or open source Portable Operating System Interface-type operating systems that employ a kernel. Generative modeling instructions included in block 200 typically includes at least some of the computer code involved in performing the inventive methods.

Peripheral device set 114 includes the set of peripheral devices of computer 101. Data communication connections between the peripheral devices and the other components of computer 101 may be implemented in various ways, such as Bluetooth® connections, Near-Field Communication (NFC) connections, connections made by cables (such as universal serial bus (USB) type cables), insertion-type connections (for example, secure digital (SD) card), connections made through local area communication networks, and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

Network module 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers, and edge servers.

End user device (EUD) 103 is any computer system that is used and controlled by an end user (for example, a customer of an enterprise that operates computer 101) and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

Remote server 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

Public cloud 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economics of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

Private cloud 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

The illustrative embodiments recognize and take into account that multi-sequence alignment (MSA) is a bioinformatics technique used to align multiple sequences such as nucleic acid sequences (DNA, RNA) or protein sequences. MSA arranges sequences such that related positions across the sequences are aligned. This alignment can contribute to understanding function and structural properties of the sequences and inferring evolutionary relationships. An example of an MSA is a set of protein sequences that belong to the same family of species.

The illustrative embodiments also recognize and take into account that phylogenetic trees are branching diagrams that depict evolutionary relationships among various biological species or other entities (e.g., protein sequences in a family) based upon similarities and differences in their physical or genetic characteristics. Phylogenetic trees can be constructed from various types of data including genetic information (nucleic acid sequences), protein sequences, and molecular markers and can be used to infer patterns of evolutionary changes.

The illustrative embodiments provide deep generative models for learning sequences based on MSAs and phylogenetic trees. The generative models are trained to predict both evolution, regression, and siblings using only information an MSA and phylogenetic tree.

FIG. 2 depicts a block diagram for generative modeling from phylogenetic data in accordance with an illustrative embodiment. Generative modeling 200 can be implemented in computing environment 100 in FIG. 1.

Generative modeling 200 begins with a nucleic acid or protein sequence 202 from a database that is used to create a multi-sequence alignment (MSA) 204. MSA 204 comprises a number of aligned sequences 206 in which related positions of nucleic acids or proteins across sequences are aligned (see FIG. 3).

From the MSA 204, generative modeling 200 generates a phylogenetic tree 208. Phylogenetic tree 208 comprises leaf nodes 210 representing the aligned sequences 206 in MSA 204 (see FIG. 4). From the leaf nodes 210, phylogenetic tree 208 can determine a number of sibling nodes 212, child nodes 214, and parent/ancestor nodes 216.

A number of machine learning models 218 generate vector representations 220 of the nucleic acid or protein sequences 202 based on phylogenetic tree 208. From the vector representations 220, a number of specialized subnetworks are able to make different types of predictions of nucleic acid or protein sequences (see FIG. 5). Sibling model 222 produces predicted sibling sequences 224. Evolution model 226 produces predicted child sequences 228. Regression model 230 produces approximated parent sequences 232 wherein parents are replaced by observed grand aunts in the phylogenetic tree 208 that are themselves leaf nodes 210 (e.g., $S_3$ in FIG. 4).

Figure 3:
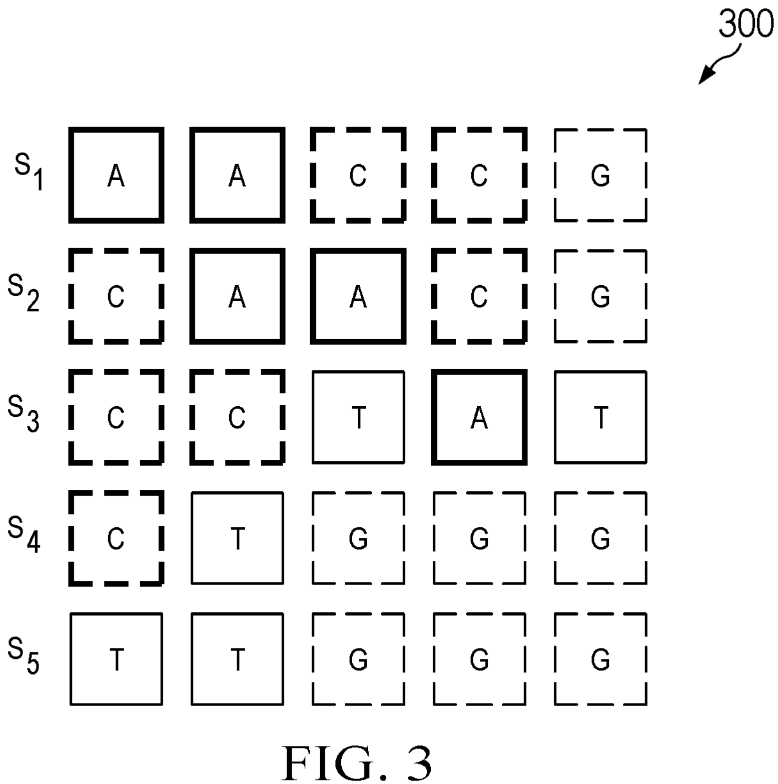
FIG. 3 depicts an example of a multi-sequence alignment (MSA) with which the illustrative embodiments can be implemented.

FIG. 3 depicts an example of a multi-sequence alignment (MSA) with which the illustrative embodiments can be implemented. MSA 300 is an example of MSA 204 in FIG. 2.

In this example, MSA 300 comprises five nucleic acid sequences $S_1$, $S_2$, $S_3$, $S_4$, $S_5$. For ease of illustration, sequences $S_1$, $S_2$, $S_3$, $S_4$, $S_5$ each contain only five nucleotides. In the present example, sequences $S_1$ and $S_1$ are similar, differing only in the first and third nucleotides. Similarly, sequences $S_4$ and $S_5$ differ only in the first nucleotide.

Figure 4:
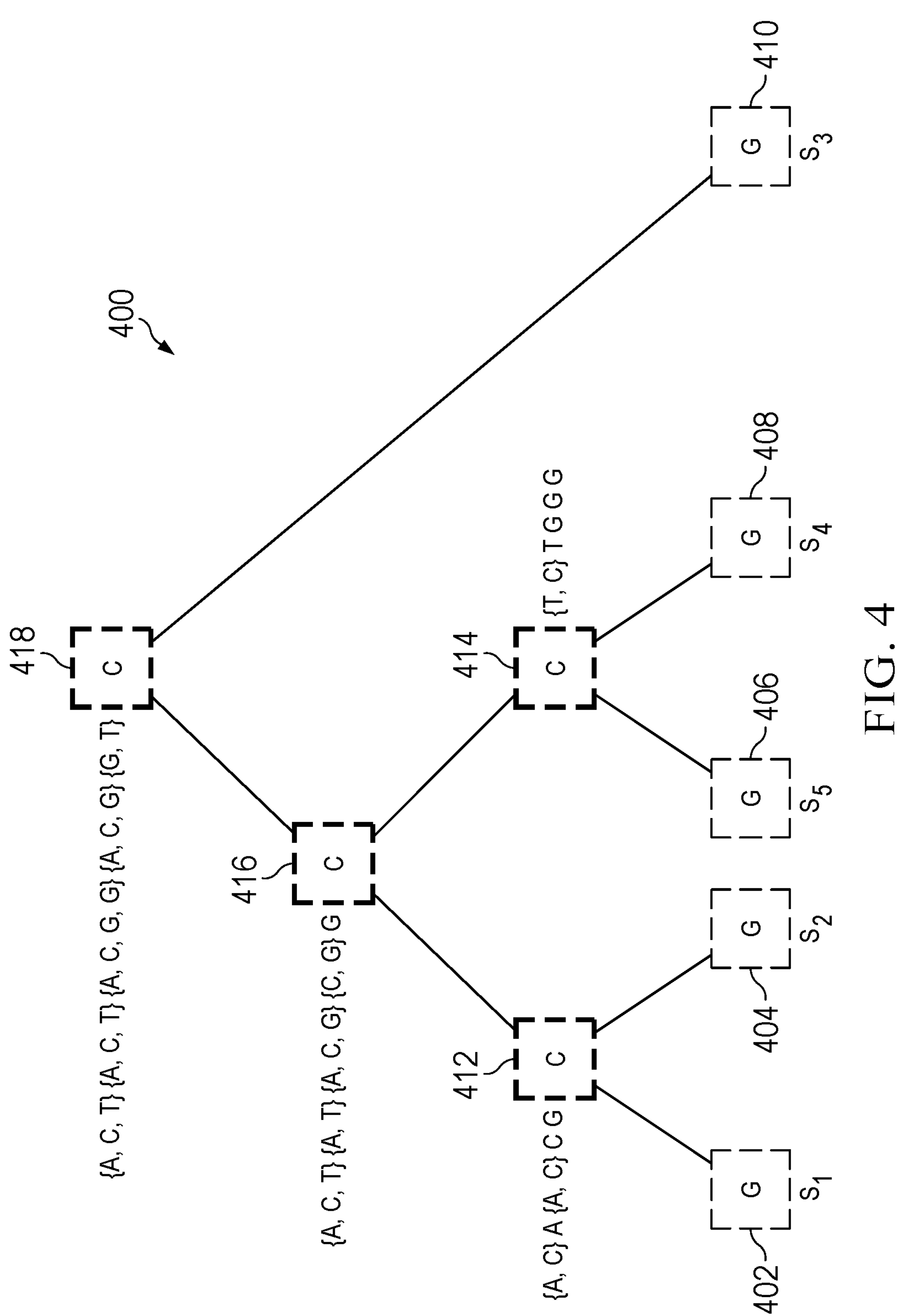
FIG. 4 depicts an example of a phylogenetic tree created from an MSA in accordance with an illustrative embodiment.

FIG. 4 depicts an example of a phylogenetic tree created from an MSA in accordance with an illustrative embodiment. Phylogenetic tree 400 is an example of phylogenetic tree 208 in FIG. 2.

In the present example, phylogenetic tree 400 comprises five leaf nodes 402, 404, 406, 408, and 410, which represent nucleic acid sequences $S_1$, $S_2$, $S_3$, $S_4$, $S_5$ in MSA 300. Phylogenetic tree 400 might be built from MSA 300 using techniques such as hierarchical clustering.

From the leaf nodes 402, 404, 406, 408, and 410 sequences at intermediate nodes 412, 414, 416, 418 are possible parents/ancestors of child sequences $S_1$, $S_2$, $S_3$, $S_4$, $S_5$. The sequences for the intermediate parent/ancestor nodes 412, 414, 416, 418 can be estimated based on Fitch's method (aka Fitch-Margoliash algorithm) in which each site in the alignment is assigned a character state based on the nucleotide or amino acid at the position. The final tree generated by Fitch's method has branch lengths that represent the minimum number of evolutionary events needed to explain differences in the sequences.

For example, for sequences $S_1$ and $S_2$ (represented by leaf nodes 402 and 404, respectively), the first and third nucleotides differ between the sequences. Therefore, the intermediate parent node 412 of leaf nodes 402, 404 has the sequence:

{A, C} A {A, C} C G

The same process is repeated for the other leaf nodes to derive parent nodes 414, 416, 418.

Given an MSA and phylogenetic tree, the illustrative embodiments provide several opportunities for generative and representational learning. Given a given parent sequence, evolution generation can estimate the most likely child sequence the parent sequence will evolve into via mutation or evolution. For a given child sequence or set of children, regression generation estimates the most likely parents of the children. Given a sequence, sibling generation estimates the most likely siblings of that given sequence.

Learning to generate evolution, regression, and sibling sequences can provide a generative model of life because species evolve via a genetic evolution process encoded in phylogenetic trees. The representation learned via those evolution and regression processes can be applied to different downstream generative and predictive tasks in various applications including, for example, drug discovery or repurposing, disease understanding, etc.

Figure 5:
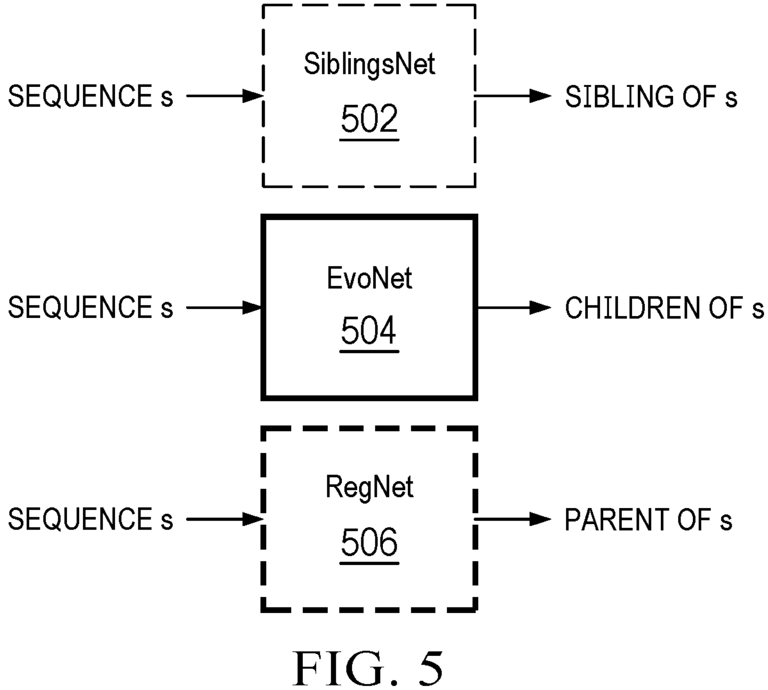
FIG. 5 depicts separate machine learning models for predicting different types of nucleic acid and protein sequences in accordance with an illustrative embodiment.

FIG. 5 depicts separate machine learning models for predicting different types of nucleic acid and protein sequences in accordance with an illustrative embodiment. Model 502, 504, 506 are examples of sibling model 222, evolution model 226, and regression model 230 in FIG. 2, respectively.

Given a nucleic acid or protein sequence, S, SiblingsNet model 502 predicts sibling sequences of S. Given the same sequence, S, EvoNet model 504 predicts children of S. Given the same sequence, S, RegNet model 506 approximates parents of S.

Each of the models 502, 504, 506 is trained with different training data derived from the MSA and phylogenetic tree. For the SiblingsNet model 502 training data is created by finding the siblings of each leaf node and creating pairs of siblings. Using the examples in FIGS. 3 and 4, the following pairs:

($S_1$, $S_2$), ($S_2$, $S_1$), ($S_4$, $S_5$), ($S_5$, $S_4$).

For RegNet model 506 training data is created by finding the closest leaf node that is a sibling of one of the parent/ancestor nodes (i.e., a grand aunt of the leaf node in question). Again, using the examples in FIGS. 3 and 4, for leaf node 408 representing sequence $S_4$, the closest leaf node that is a sibling of one of 408's ancestors is leaf node 410 ($S_3$). As such, lead node 410 is considered an approximation of 408's parent (node 414). Therefore, for RegNet model 506, the input pair is ($S_4$, $S_3$).

The training data for EvoNet model 504 uses the same training data created for RegNet model 506 but reverses the order of the node in the input pair. Therefore, using the same example above, the input pair for EvoNet model 504 would be ($S_3$, $S_4$).

Models 502, 504, 506 rely on different neural network architectures, depending on the tasks at hand. For generative modeling, transformers with condition generation heads can be used as the network structure. Such models incorporate task-specific heads to generate output sequences according to specific input conditions or context. The transformer's decoder can be extended with additional conditioning mechanism depending on the specific task at hand. Examples include Bayesian additive regression trees (BART), Text-to-Text Transform Transformer (T5), etc.

For generative modeling, the models 502, 504, 506 are trained by supplying them a pair of input and output sequences. The training objective is to minimize the cross entropy loss of the sequence generation task. Cross entropy loss is common loss function used in machine learning which measure the dissimilarity between the predicted probability and the true probability.

For sequence representation learning, transformers with masked language model (MLM) heads can be used as the network structure. When training transformers with MLM heads a subset of tokens in the input is masked or replaced, and the model is trained to predict the original values of the masked token based on surrounding context. To avoid trivial prediction of exact match tokens and encourage the models to learn the evolution/regression, the illustrative embodiments ignore tokens in the output sequence that have an exact match in the input sequence in the MSA.

For example, the model might be supplied with the input sequence:

ACCGT and the output sequence:

AGXGD

Because the first and fourth tokens are the same in both sequences they are masked, and the output sequence is modified to:

-GX-D

And the model is trained using the modified output sequence. Again, the objective of learning is to minimize the cross entropy loss of the prediction.

Figure 6:
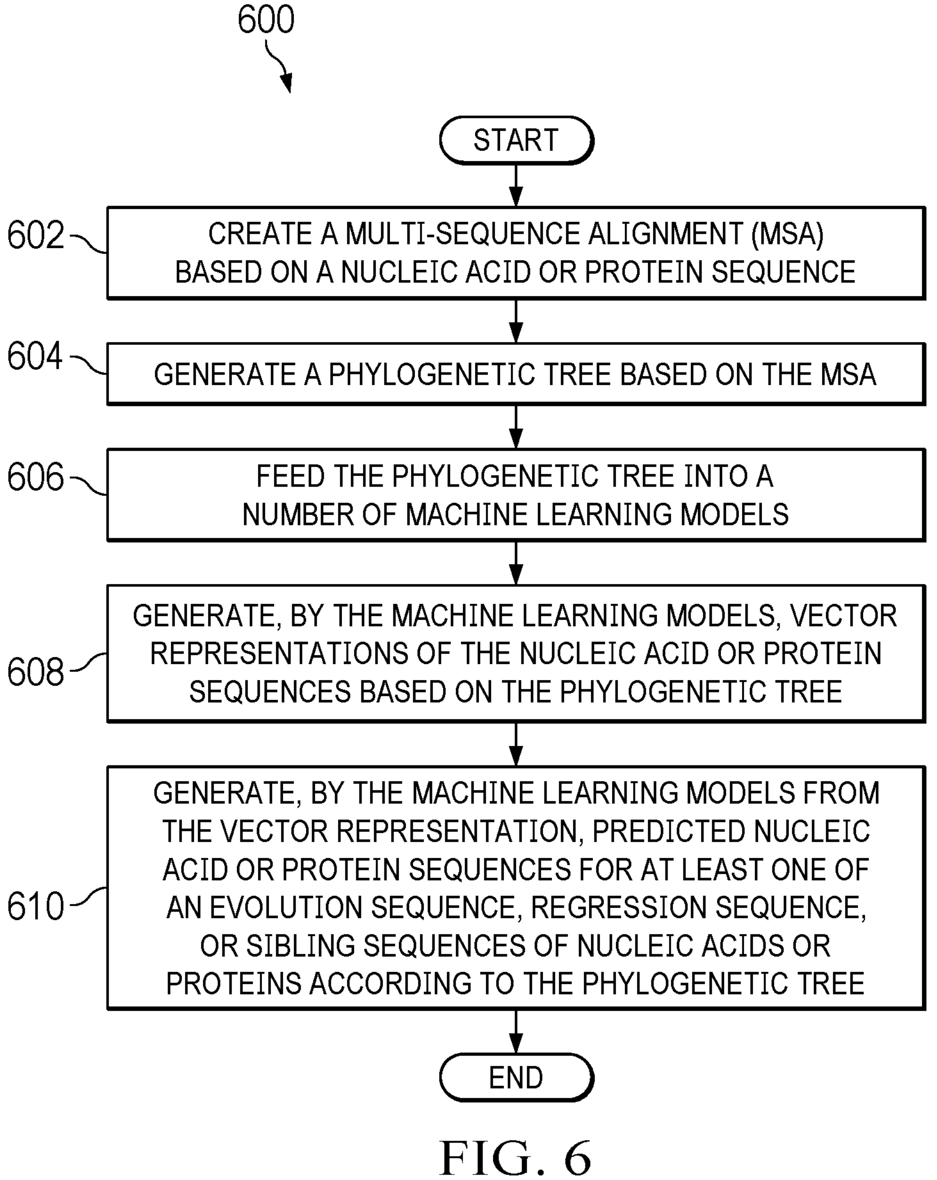
FIG. 6 depicts a flowchart for generative modeling from phylogenetic data in accordance with an illustrative embodiment.

FIG. 6 depicts a flowchart for generative modeling from phylogenetic data in accordance with an illustrative embodiment. Process 600 can be carried out in computing environment 100 in FIG. 1.

Process 600 begins by creating a multi-sequence alignment (MSA) based on a number of nucleic acid or protein sequences (step 602) and generating a phylogenetic tree based on the MSA (step 604).

Process 600 feeding the phylogenetic tree into a number of machine learning models (step 606), which generate vector representations of the nucleic acid or protein sequences based on the phylogenetic tree (step 608). The machine learning models might comprise at least one of transformers with condition generation heads or transformers with masked language model heads.

The machine learning models generate from the vector representation predicted nucleic acid or protein sequences for at least one of an evolution sequence, regression sequence, or sibling sequences of nucleic acids or proteins according to the phylogenetic tree (step 610). During training, the machine learning models might be provided an input nucleic acid or protein sequence and an output nucleic acid or protein sequence and then minimize cross entropy loss of sequence generation tasks. Alternatively, during training, the machine learning models might be provided an input nucleic acid or protein sequence and an output nucleic acid or protein sequence and ignore tokens in the output sequence that have matching tokens in the input nucleic acid or protein sequence. Process 600 then ends.

Figure 7:
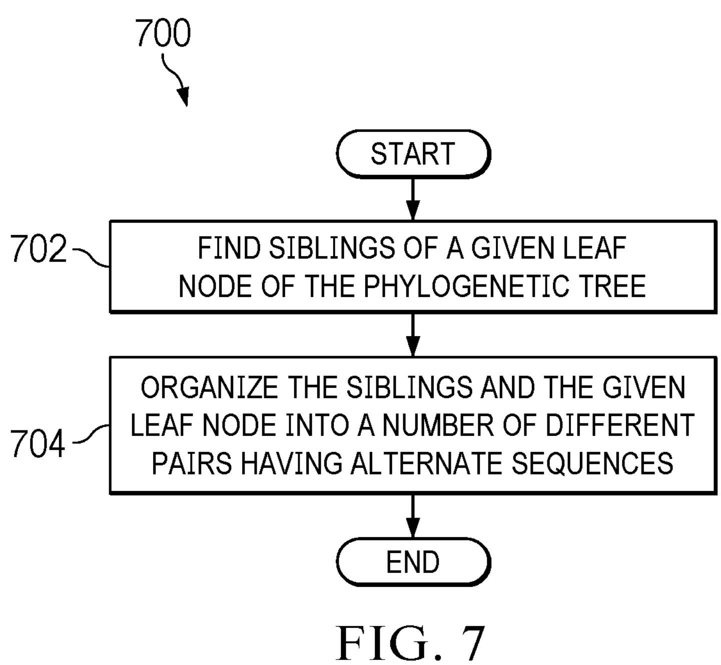
FIG. 7 depicts a flowchart for creating training data for predicting sibling sequences in accordance with an illustrative embodiment.

FIG. 7 depicts a flowchart for creating training data for predicting sibling sequences in accordance with an illustrative embodiment. Process 700 can be applied when a machine learning model predicts sibling sequences of nucleic acids or proteins in step 610 in FIG. 6.

Process 700 begins by finding siblings of a given leaf node of the phylogenetic tree (step 702). Process 700 then organizes the siblings and the given leaf node into a number of different pairs having alternate sequences (step 704). Process 700 then ends.

Figure 8:
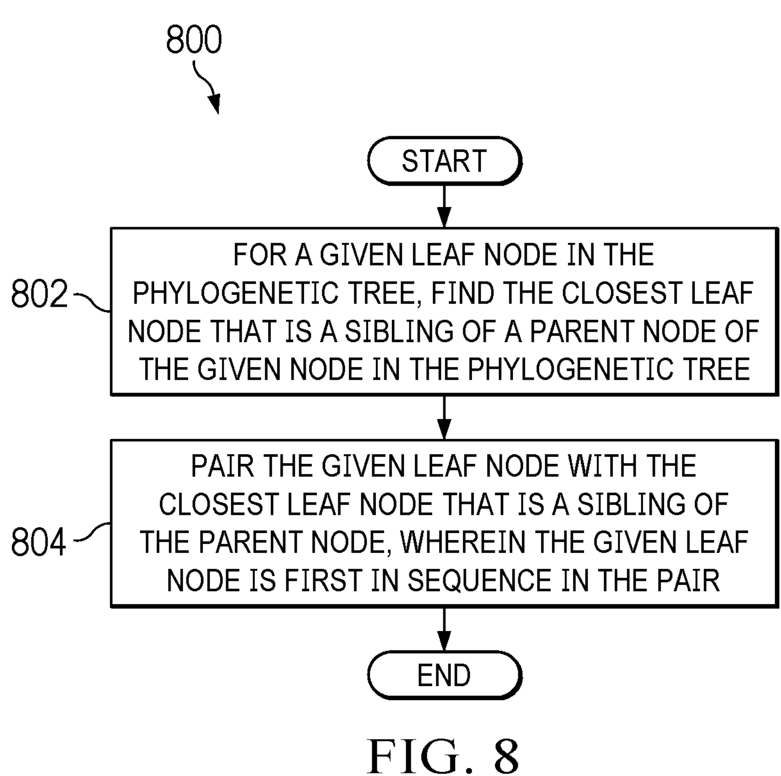
FIG. 8 depicts a flowchart for creating training data for predicting regression sequences in accordance with an illustrative embodiment.

FIG. 8 depicts a flowchart for creating training data for predicting regression sequences in accordance with an illustrative embodiment. Process 800 can be applied when a machine learning model predicts regression sequences of nucleic acids or proteins in step 610 in FIG. 6.

For a given leaf node in the phylogenetic tree, process 800 begins by finding the closest leaf node that is a sibling of a parent node of the given node in the phylogenetic tree (step 802). Process 800 pairs the given leaf node with the closest leaf node that is a sibling of the parent node, wherein the given leaf node is first in sequence in the pair (step 804). Process 800 then ends.

Figure 9:
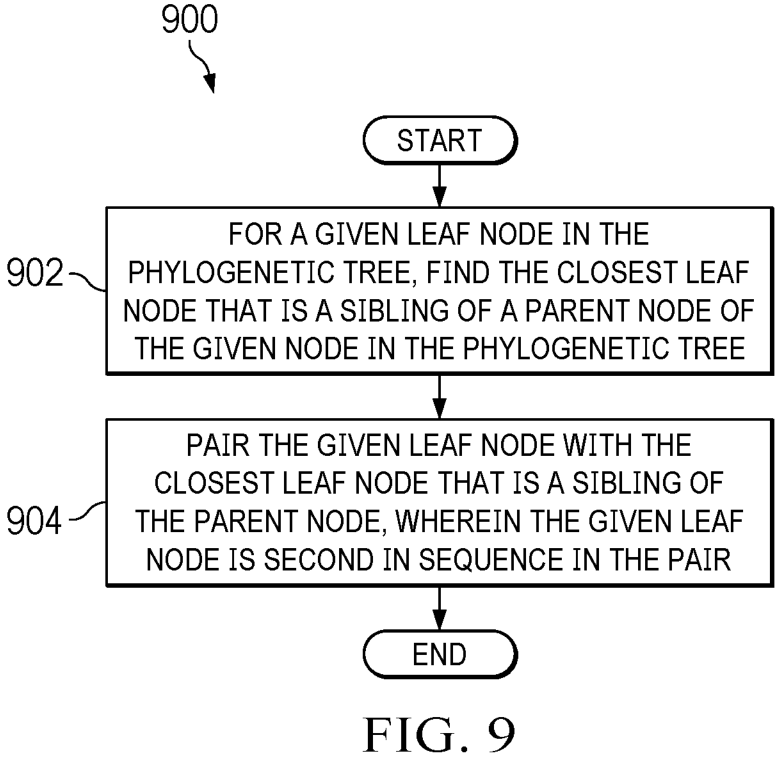
FIG. 9 depicts a flowchart for creating training data for predicting evolution sequences in accordance with an illustrative embodiment.

FIG. 9 depicts a flowchart for creating training data for predicting evolution sequences in accordance with an illustrative embodiment. Process 900 can be applied when a machine learning model predicts evolution sequences of nucleic acids or proteins in step 610 in FIG. 6.

For a given leaf node in the phylogenetic tree, process 900 begins by finding the closest leaf node that is a sibling of a parent node of the given node in the phylogenetic tree (step 902). Process 900 pairs the given leaf node with the closest leaf node that is a sibling of the parent node, wherein the given leaf node is second in sequence in the pair (step 904). Process 900 then pairs.

As used herein, a "number of," when used with reference to objects, means one or more objects. For example, a "number of different types of networks" is one or more different types of networks.

Further, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

As used herein, a "computer instruction," or "computer program", means one step or a set of steps that includes information on how to operate, perform, or maintain particular computer software or hardware. For example, a "computer instruction" can be a computer program instruction in the form of lines of code or source code that are executable by a computer system.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component can be configured to perform the action or operation described. For example, the component can have a configuration or design for a structure that provides the component an ability to perform the action or operation that is described in the illustrative examples as being performed by the component. Further, to the extent that terms "includes", "including", "has", "contains", and variants thereof are used herein, such terms are intended to be inclusive in a manner similar to the term "comprises" as an open transition word without precluding any additional or other elements.

The descriptions of the various embodiments of the present disclosure have been presented for purposes of illustration but are not intended to be exhaustive or limited to the embodiments disclosed. Not all embodiments will include all of the features described in the illustrative examples. Further, different illustrative embodiments may provide different features as compared to other illustrative embodiments. Many modifications and variations will be apparent to those of ordinary skill in the art without departing from the scope and spirit of the described embodiment. The terminology used herein was chosen to best explain the principles of the embodiment, the practical application or technical improvement over technologies found in the marketplace, or to enable others of ordinary skill in the art to understand the embodiments disclosed here.

What is claimed is:

1. A computer-implement method of generative modeling from phylogenetic data, the method comprising:

using a number of processors to perform:

creating a multi-sequence alignment (MSA) based on a nucleic acid or protein sequence;

generating a phylogenetic tree based on the MSA;

feeding the phylogenetic tree into a number of machine learning models;

generating, by the machine learning models, vector representations of the nucleic acid or protein sequences based on the phylogenetic tree; and generating, by the machine learning models from the vector representation, complete predicted nucleic acid or protein sequences for at least one of an evolution sequence, regression sequence, or sibling sequences of nucleic acids or proteins according to the phylogenetic tree.

2. The method of claim 1, wherein the machine learning models comprise at least one of:

transformers with condition generation heads; or transformers with masked language model heads.

3. The method of claim 1, wherein, during training, the machine learning models are provided an input nucleic acid or protein sequence and an output nucleic acid or protein sequence and minimize cross entropy loss of sequence generation tasks.

4. The method of claim 1, wherein, during training, the machine learning models are provided an input nucleic acid or protein sequence and an output nucleic acid or protein sequence and ignore tokens in the output sequence that have matching tokens in the input nucleic acid or protein sequence.

5. The method of claim 1, further comprising creating training data for predicting sibling sequences by:

finding siblings of a given leaf node of the phylogenetic tree; and organizing the siblings and the given leaf node into a number of different pairs having alternate sequences.

6. The method of claim 1, further comprising creating training data for predicting regression sequences by:

for a given leaf node in the phylogenetic tree, finding the closest leaf node that is a sibling of a parent node of the given node in the phylogenetic tree; and pairing the given leaf node with the closest leaf node that is a sibling of the parent node, wherein the given leaf node is first in sequence in the pair.

7. The method of claim 1, further comprising creating training data for predicting evolution sequences by:

for a given leaf node in the phylogenetic tree, finding the closest leaf node that is a sibling of a parent node of the given node in the phylogenetic tree; and pairing the given leaf node with the closest leaf node that is a sibling of the parent node, wherein the given leaf node is second in sequence in the pair.

8. A system for generative modeling from phylogenetic data, the system comprising:

a storage device that stores program instructions;

one or more processors operably connected to the storage device and configured to execute the program instructions to cause the system to:

create a multi-sequence alignment (MSA) based on a nucleic acid or protein sequence;

generate a phylogenetic tree based on the MSA;

feed the phylogenetic tree into a number of machine learning models;

generate, by the machine learning models, vector representations of the nucleic acid or protein sequences based on the phylogenetic tree; and generate, by the machine learning models from the vector representation, complete predicted nucleic acid or protein sequences for at least one of an evolution sequence, regression sequence, or sibling sequences of nucleic acids or proteins according to the phylogenetic tree.

9. The system of claim 8, wherein the machine learning models comprise at least one of:

transformers with condition generation heads; or transformers with masked language model heads.

10. The system of claim 8, wherein, during training, the machine learning models are provided an input nucleic acid or protein sequence and an output nucleic acid or protein sequence and minimize cross entropy loss of sequence generation tasks.

11. The system of claim 8, wherein, during training, the machine learning models are provided an input nucleic acid or protein sequence and an output nucleic acid or protein sequence and ignore tokens in the output sequence that have matching tokens in the input nucleic acid or protein sequence.

12. The system of claim 8, wherein the program instructions further cause the system to create training data for predicting sibling sequences by:

finding siblings of a given leaf node of the phylogenetic tree; and organizing the siblings and the given leaf node into a number of different pairs having alternate sequences.

13. The system of claim 8, wherein the program instructions further cause the system to create training data for predicting regression sequences by:

for a given leaf node in the phylogenetic tree, finding the closest leaf node that is a sibling of a parent node of the given node in the phylogenetic tree; and pairing the given leaf node with the closest leaf node that is a sibling of the parent node, wherein the given leaf node is first in sequence in the pair.

14. The system of claim 8, wherein the program instructions further cause the system to create training data for predicting evolution sequences by:

for a given leaf node in the phylogenetic tree, finding the closest leaf node that is a sibling of a parent node of the given node in the phylogenetic tree; and pairing the given leaf node with the closest leaf node that is a sibling of the parent node, wherein the given leaf node is second in sequence in the pair.

15. A computer program product for generative modeling from phylogenetic data, the computer program product comprising:

a persistent storage medium having program instructions configured to cause one or more processors to:

create a multi-sequence alignment (MSA) based on a nucleic acid or protein sequence;

generate a phylogenetic tree based on the MSA;

feed the phylogenetic tree into a number of machine learning models;

generate, by the machine learning models, vector representations of the nucleic acid or protein sequences based on the phylogenetic tree; and generate, by the machine learning models from the vector representation, complete predicted nucleic acid or protein sequences for at least one of an evolution sequence, regression sequence, or sibling sequences of nucleic acids or proteins according to the phylogenetic tree.

16. The computer program product of claim 15, wherein, during training, the machine learning models are provided an input nucleic acid or protein sequence and an output nucleic acid or protein sequence and minimize cross entropy loss of sequence generation tasks.

17. The computer program product of claim 15, wherein, during training, the machine learning models are provided an input nucleic acid or protein sequence and an output nucleic acid or protein sequence and ignore tokens in the output sequence that have matching tokens in the input nucleic acid or protein sequence.

18. The computer program product of claim 15, wherein the program instructions are further configured to cause the processors to create training data for predicting sibling sequences by:

finding siblings of a given leaf node of the phylogenetic tree; and organizing the siblings and the given leaf node into a number of different pairs having alternate sequences.

19. The computer program product of claim 15, wherein the program instructions are further configured to cause the processors to create training data for predicting regression sequences by:

for a given leaf node in the phylogenetic tree, finding the closest leaf node that is a sibling of a parent node of the given node in the phylogenetic tree; and pairing the given leaf node with the closest leaf node that is a sibling of the parent node, wherein the given leaf node is first in sequence in the pair.

20. The computer program product of claim 15, wherein the program instructions are further configured to cause the processors to create training data for predicting evolution sequences by:

for a given leaf node in the phylogenetic tree, finding the closest leaf node that is a sibling of a parent node of the given node in the phylogenetic tree; and pairing the given leaf node with the closest leaf node that is a sibling of the parent node, wherein the given leaf node is second in sequence in the pair.

* * * * *